United States Patent
Schlegl (10) Patent No.: US 7,651,848 B2
(45) Date of Patent: Jan. 26, 2010

(54) METHOD FOR REFOLDING A PROTEIN (75) Inventor: Robert Schlegl, Vienna (AT)

(73) Assignee: Boehringer Ingelheim RCV GmbH & Co. KG, Vienna (AT)

( * ) Notice: Subject to any disclaimer, the term of this patent is extended or adjusted under 35 U.S.C. 154(b) by 0 days.

(21) Appl. No.: 11/695,950

(22) Filed: Apr. 3, 2007

(65) Prior Publication Data

US 2007/0238860 A1 Oct. 11, 2007

(30) Foreign Application Priority Data

Apr. 10, 2006 (EP) .................................. 06112443

(51) Int. Cl.
*C12P 21/06* (2006.01)
(52) U.S. Cl. ..................................... 435/69.1; 530/417
(58) Field of Classification Search ................. 435/69.1; 530/417
See application file for complete search history.

(56) References Cited

U.S. PATENT DOCUMENTS

| 4,999,422 | A | 3/1991 | Galliher |
| 5,917,018 | A | 6/1999 | Thogersen |
| 7,060,460 | B2 * | 6/2006 | Necina et al. ............... 435/69.1 |
| 2004/0116663 | A1 | 6/2004 | Buus et al. |

FOREIGN PATENT DOCUMENTS

WO 01/55174 A2 8/2001

OTHER PUBLICATIONS

European Search Report EP06112443 dated Jul. 25, 2006.
C. Machold, et al., "Continuous matrix assisted refolding of A-lactalbumin by ion exchange chromatography with recycling of aggregates combined with ultrafiltration". Journal of Chromatography, vol. 1080, Vo. 1, Jul. 1, 2005, pp. 29-42.
R. Schlegl, et al., "Continuous matrix-assisted refolding of proteins". Journal of Chromatography, vol. 1009, No. 1-2, Aug. 15, 2003, pp. 119-132.
Horwich, A.L., Neupert, W. and Hartl, F.U. (1990) Protein-catalyzed protein folding. Trends Biotechnol, 8, 126-131.
Noiva, R. (1994) Enzymatic catalysis of disulfide formation. Protein Expr Purif, 5, 1-13.
Schoenbrunner, E.R., Schmid, F.X., Mayer, S., Tropschug, M., Fischer, G. and Takahashi, N. (1992) Peptidyl-prolyl cis-trans isomerase improves the efficiency of protein disulfide isomerase as a catalyst of protein folding catalysis of protein folding by cyclophilins from different species. Proc Natl Acad Sci U S A, 89, 4510-4513.
Lilie, H., Lang, K., Rudolph, R., Buchner, J., Schonbrunner, E.R., Schmid, F.X., Mayer, S., Tropschug, M., Fischer, G. and Takahashi, N. (1993) Prolyl isomerases catalyze antibody folding in vitro. Protein Sci, 2, 1490-1496.
Jaeger, M., Pluckthun, A., Yang, H.P., Zhong, H.N., Zhou, H.M., Lilie, H., Lang, K., Rudolph, R., Buchner, J., Schonbrunner, E.R., Schmid, F.X., Mayer, S., Tropschug, M., Fischer, G. and Takahashi, N. (1997) The rate-limiting steps for the folding of an antibody scFv fragment. FEBS Lett, 418, 106-110.
Yang, H.P., Zhong, H.N., Zhou, H.M., Lilie, H., Lang, K., Rudolph, R., Buchner, J., Schonbrunner, E.R., Schmid, F.X., Mayer, S., Tropschug, M., Fischer, G. and Takahashi, N. (1997) Catalysis of the refolding of urea denatured creatine kinase by peptidyl-prolyl cis-trans. Biochim Biophys Acta, 1338, 147-150.
Kane, J.F. and D.L., H. (1988) Formation of recombinant inclusion bodies in *Escherichia coli*. TIBTECH, 6, 95-100.
Buchner, J. and Rudolph, R. (1991) Routes to active proteins from transformed microorganisms. Current Opinion Biotechnology, 2, 532-538.
Halenbeck, R., Kawasaki, E., Wrin, J. and Koths, K. (1989) Renaturation and purification of biologicla active recombinant human macrophage colony-stimulating factor expressed in *E.coli*. Biotechnology, 7, 710-715.
Kiefhaber, T., Rudolph, R., Kohler, H.H. and Buchner, J. (1991) Protein aggregation in vitro and in vivo: a quantitative model of the kinetic competition between folding and aggregation. Biotechnology (N Y), 9, 825-829.
Chen, L., Wildegger, G., Kiefhaber, T., Hodgson, K.O. & Doniach, S. Kinetics of lysozyme refolding: structural characterization of a non-specifically collapsed state using time-resolved X-ray scattering. J Mol Biol 276, 225-237. (1998).
Onda, M. & Hirose, M. Refolding mechanism of ovalbumin: Investigation by using a starting urea-denatured disulfide isomer with mispaired Cys367-Cys382. J Biol Chem 23, 23 (2003).
Pradeep, L. & Udgaonkar, J.B. Differential salt-induced stabilization of structure in the initial folding intermediate ensemble of barstar. J Mol Biol 324, 331-347. (2002).

(Continued)

*Primary Examiner*—Tekchand Saidha
(74) *Attorney, Agent, or Firm*—Michael P. Morris; Mary-Ellen M. Devlin; Anthony P. Bottino (57) ABSTRACT

A method for refolding a protein by mixing a protein solution with a refolding buffer at mixing conditions that approximate ideal mixing. The method can be carried out batch wise, in a fed-batch mode or continuously with on-line solubilization of inclusion bodies.

15 Claims, 6 Drawing Sheets

OTHER PUBLICATIONS

Lee, J.C., Engman, K.C., Tezcan, F.A., Gray, H.B. & Winkler, J.R. Structural features of cytochrome c' folding intermediates revealed by fluorescence energy-transfer kinetics. Proc Natl Acad Sci U S A 99, 14778-14782. (2002).

O'Neill, J.C., Jr. & Robert Matthews, C. Localized, Stereochemically sensitive hydrophobic packing in an early folding intermediate of dihydrofolate reductase from *Escherichia Coli*. J Mol Biol 295, 737-744. (2000).

Arai, M., Ito, K., Inobe, T., Kuwajima, K., Fast compaction of α-lactalbumin during folding studied by stopped-flow X-ray scattering. J Mol Biol 321, 121-132. (2002).

Ptitsyn, O.B. Molten globule and protein folding. Advan. Protein Chem. 47, 83-217. (1995).

Lilie, H., Schwarz, E. and Rudolph, R. (1998) Advances in refolding of proteins produced in *E. coli*. Curr Opin Biotechnol, 9, 497-501.

Clark, E.D. (2001) Protein refolding for industrial processes. Curr Opin Biotechnol, 12, 202-207.

Yoshi, H., Furuta, T., Yonehara, T., Ito, D. and Linko, P. (2001) Refolding of denatured and reduced lysozyme with cysteine/cystine red/ox solution in diafiltration. J Chem Eng Japan, 34, 211-215.

Buchner, J., Brinkmann, U. and Pastan, I. (1992) Renaturation of a single-chain immunotoxin facilitated by chaperones and protein disulfide isomerase, Biotechnology (N Y), 10, 682-685.

Carlson, J.D. and Yarmush, M.L. (1992) Antibody assisted protein refolding. Biotechnology (N Y), 10, 86-91.

Guise, A.D. and Chaudhuri, J.B. (1998) Recovery and reuse of the molecular chaperone GroEL for in vitro protein refolding. Biotechnol Prog, 14, 343-346.

Kohler, R.J., Preuss, M. and Miller, A.D. (2000) Design of a molecular chaperone-assisted protein folding bioreactor. Biotechnol Prog, 16, 671-675.

Shimizu, H., Fujimoto, K. and Kawaguchi, H. (2000) Renaturation of reduced ribonuclease A with a microsphere-induced refolding system. Biotechnol Prog, 16, 248-253.

Katoh, S. and Katoh, Y. (2000) Continuous refolding of lysozyme with fed-batch addition of denatured protein solution. Process Biochemistry 35, 1119-1124.

Phadtare, S., Fisher, M.T. and Yarbrough, L.R. (1994) Refolding and release of tubulins by a functional immobilized groEL column. Biochim Biophys Acta, 1208, 189-192.

Altamirano, M.M., Golbik, R., Zahn, R., Buckle, A.M. and Fersht, A.R. (1997) Refolding chromatography with immobilized mini-chaperones. Proc Natl Acad Sci U S A, 94, 3576-3578.

Altamirano, M.M., Garcia, C., Possani, L.D. and Fersht, A.R. (1999) Oxidative refolding chromatography: folding of the scorpion toxin Cn5. Nat Biotechnol, 17, 187-191.

Preston, N.S., Baker, D.J., Bottomley, S.P. and Gore, M.G. (1999) The production and characterization of an immobilised chaperonin system. Biochim Biophys Acta, 1426, 99-109.

Terashima, M., Suzuki, K., Katoh, S., (1996). Effective refolding of fully reduced lysozyme with a flow-type reactor. Process Biochem., 31, 341-345.

Buswell, M.A., Ebtinger, M., Vertés, A.A., Middelberg, A.P.J., (2002). Effect of operating variables on the yield of recombinant trypsinogen for a pulse-fed dilution-refolding reactor. Biotechnol. Bioeng., 77, 435-444.

Ram, K., Vickroy, B., Lamb, K., Slater, N.K., Dennis, J.S., Duffy, L.E., (2000). Mixing in process vessels used in biopharmaceutical manufacturing. Biotech. Prog., 16, 244-247.

Fischer, B., Perry, B., Summer, I., Goodenough, P., (1992). A novel sequential procedure to enhance the renaturation of recombinant protein from *E.coli* inclusion bodies. Prot. Eng. 5, 593-596.

Dong, X.Y., Shi, G.Q., Li, W., Sun, Y. (2004). Modeling and Simulation of Fed-Batch Protein Refolding Process. Biotechnol. Prog. 2004, 20, 1213-1219.

N. Kotlarski, B.K. O'Neill, G.L. Francis., "Design Analysis for Refolding Monomeric Protein". A.P.J. Middelberg, (1997), AIChE J., 43, 2123.

Clark, E.D., et al. "Inhibition of Aggregation Side Reactions During in Vitro Protein Folding". Methods in Enzymology, vol. 309, p. 217-236. (1999).

Permyakov, E.A., Berliner, L.J., (2000). Alpha-Lactalbumin: structure and function. FEBS Lett., 473. 269-274.

Ewbank, J.J., Creighton, T.E., (1993). Structural characterization of the disulfide folding intermediates of bovine alpha-lactalbumin. Biochemistry, 32, 3694-3707.

Wu, L.C., Schulman, B.A., Peng, Z.Y., Kim, P.S., (1996). Disulfide determinants of calcium-induced packing in alpha-lactalbumin. Biochemistry, 35, 859-863.

* cited by examiner

METHOD FOR REFOLDING A PROTEIN

This application claims priority benefit to EP 06 112 443, dated Apr. 10, 2006, the entirety of which is incorporated herein.

The invention relates to the field of recombinant protein production

Proteins for industrial applications, e.g. for use as biopharmaceuticals or fine chemicals, are either obtained by extraction and purification from a natural source, such as a plant or animal tissue or microorganisms, or by means of recombinant DNA technology.

To produce a recombinant protein, the cDNA encoding the protein of interest is inserted into an expression vector and the recombinant vector is transformed into host cells, which are grown to express the protein. The host cells may be selected from microorganisms such as bacteria, yeast or fungi, or from animal or plant cells.

Expression of a recombinant protein is a complex event. To obtain the correct conformation, the protein is associated with so-called "folding helper proteins" and enzymes. The folding helper proteins, also termed "chaperones" or "minichaperones", interact in a complex way so that the protein regains its native conformation after passing through various intermediate states. Some of the intermediate states may be quite stable. Enzymes involved in protein maturation either catalyze the rapid formation of disulfide bridges (1; 2), the isomerization of prolyl-peptide linkages (3-6) or more complex modifications, such as the truncation of the protein, side chain modifications or modifications of the N- and C-terminus. When a protein is efficiently overexpressed, the production of the nascent peptide chain occurs faster than the folding of the protein. For some proteins, an intermediate state may also form aggregates (in the following, the term "intermediate" forms also encompasses aggregate forms). Overall, aggregate formation occurs much faster than the complete folding of a protein (7; 8).

In expression systems, in which such conditions are present, the protein is deposited in the cells in a paracrystalline form, so-called "inclusion bodies", also termed "refractile bodies".

Since the protein, when present in the form of insoluble inclusion bodies, is shielded from enzymatic attack like proteolysis, it cannot interfere with the physiology of the cells. Therefore, recombinant DNA technology has taken advantage of this aberrant way of protein secretion, e.g. for the production of the proteins that are toxic for the cells (9).

Various steps have to be taken to obtain a protein from host cells, in which it is accumulated in a denatured form, i.e. a conformational state without biological activity, in its correctly refolded form. For example, bacterial cells carrying inclusion bodies are disintegrated, the inclusion bodies harvested by centrifugation and then dissolved in a buffer containing a chaotropic agent. The denatured protein is then transferred into an environment that favors the recovery of its native conformation. Before adopting its native state, the protein undergoes a transition through various semi-stable intermediates. Since intermediates in the early stages of the folding pathway have highly exposed hydrophobic domains, which are prone to associate, they tend to form aggregates. Obviously, intramolecular interactions are concentration-independent, whereas intermolecular interactions are concentration-dependent. The higher the protein concentration, the higher the risk of intermolecular misfolding, and vice versa. In principle, refolding, also termed "renaturation", may be considered as a race against aggregate formation, which usually follows second or higher order reaction kinetics, while refolding of the protein follows first order reaction kinetics (10).

A protein can be refolded from its denatured conformation to the correctly folded conformation by transferring it into an environment that favors the change to the native conformation. During this rearrangement, the protein passes through several intermediate conformational states, which are prone to form aggregates. Depending on the individual protein and on the environmental conditions, the aggregates may precipitate. Independent of whether the aggregates remain soluble or whether they precipitate, this process leads to dramatic losses in the yield of correctly folded protein.

During a folding reaction, several characteristic conformations are formed. Although the transition from one conformation to another is smooth and a characterization of the distinct conformations is not available yet, similar states have been reported for different proteins. Immediately after initiation of the folding reaction, the unfolded protein collapses and a partly structured intermediate state is formed. This change in conformation is called burst phase and appears in the sub millisecond time scale. Rapid changes in spectroscopic properties, such as fluorescence and far UV-CD are due to the molecular collapse of the protein. For lysozyme, molecular compaction and formation of globular shape was detected with small angle X-ray scattering and tryptophan fluorescence (11). Other examples of proteins where a burst phase was detected are ovalbumin (12), barstar (13), cytochrom C (14), dihydrofolat reductase (15) and α-lactalbumin (16). After the burst phase, a more compact structure is formed, the 'molten globule' intermediate. The molten globule is defined as state with native-like secondary structure but fluctuating tertiary structure (17). It was proposed as a common intermediate in folding pathways and a number of proteins pass through a molten globule structure during folding. Intermediates in early folding steps cannot be detected, either due to very rapid or very little structural changes. In later folding events, reorganization of tertiary contacts takes place. These reactions are slow compared to formation of secondary and tertiary structure. They comprise generation and reshuffling of disulfide bonds, proline isomerization and domain pairing. Disulfide bond intermediates can be detected for example with reversed phase chromatography. Association of native monomers to biologically active oligomers is the final step in the case of larger proteins.

With some currently available methods, refolding of proteins is achieved either by diluting the protein in a refolding buffer in a batch or continuous mode (18-20). In these methods, batch wise dilution results in highly diluted protein solutions and therefore large process volume, which often is the bottleneck in industrial processes.

In another approach the naturally occurring folding pathway is simulated by adding chaperons and/or minichaperons, and/or enzymes that catalyze certain steps in the in vivo folding pathway (2; 21-25). Complex refolding reactor systems comprising series of tanks have been designed to improve the refolding reaction (26).

In another approach, the helper proteins and enzymes are immobilized to a solid phase. Then the protein solution is passed over a so-called "Packed Bed" that contains the immobilized helper proteins and/or helper enzymes, whereby the protein is folded into its native conformation (27-30). Since the folding helper proteins and enzymes must be present in a stoichiometric ratio, this process requires almost the same amount of helper proteins, which in turn have to be produced by recombinant DNA technology, as the finally obtained protein of interest. In addition, to improve folding, the helper proteins are usually fused to the protein of interest, which requires further processing of the fusion protein. For these reasons, this strategy is very cost intensive and not applicable on an industrial scale.

WO 02/057296 discloses an on-line method for refolding a protein by dilution and subsequent separation. The solution containing unfolded protein is diluted with refolding buffer by mixing in a mixing chamber and the output of this dilution step is directly loaded onto the separation device, e.g. a chromatographic column. By optionally varying the length of the tubing between the mixing chamber and the column, the time for refolding the protein in solution—before it is bound to the column—can be adjusted. This system is limited to proteins with fast refolding kinetics and to proteins with low requirements as regards adjusting the conditions of the separation step to those of the antecedent refolding step.

Dilution of the unfolded protein with the refolding buffer using a flow-type reactor was described by Terashima et al (31): Denatured lysozyme is continuously diluted in a small mixing unit and directed to a packed column with a flow that closely approaches a plug flow. The achieved refolding efficiencies in the flow type reactor are hardly superior to those of a batch system.

Among the known refolding strategies, dilution is still the simplest methodology. In industrial scale applications, dilution is commonly used for refolding of recombinant proteins, expressed as inclusion bodies. Typically, dilution is carried out in one step by mixing/diluting the solution containing solubilized protein with a diluent containing a solubilizing agent in an amount necessary to reach the optimal level of dilution. When the concentration of solubilizing agent is below a certain threshold level, the protein start to regain its biologically active three-dimensional conformation. Depending on the specific protein and the chosen folding conditions, refolding begins within milliseconds to seconds. In this initial burst phase, the protein is highly susceptible to aggregation. To minimize aggregation, the protein concentration has to be kept low. After this initial refolding phase, the protein forms into a more compact structure. This intermediate structure, which is sometimes termed 'molten globule', is defined as a state with a secondary structure that resembles that of the native protein and that is less susceptible to aggregation. Complete refolding, including formation of disulfide bonds, proline isomerization and domain pairing may take hours and up to several days.

Usually, such dilution is carried out as a so-called "batch" dilution, in which the diluent is added in a defined volume, the "batch", to the unfolded protein solution. Batch dilution has many disadvantages when carried out at large scale. In commercial protein purification methods, depending on the dilution rate, the total volumes being handled at the same time can be very large, usually between several hundreds or thousand liters. In such processes, variations in refolding efficiency are caused by ill-defined operating variables with regard to feed rate and mixing, which result in non-robust processes during scale-up with (32).

During batch refolding, all of the protein in the reactor is transiently present in the form of reactive intermediates, resulting in a brief period of aggregation. Therefore, optimum operation occurs at extremely low overall protein concentration. Additionally, refolding a protein in large volumes by batch dilution may cause some re-aggregation of the protein, probably because the solution, at least as initially present in batch dilutions, is not homogeneous. This may result in a lower net yield of refolded protein. The non-homogeneity of the solution in batch dilutions results from the difficulty in timely achieving "ideal" mixing conditions, which are required for obtaining homogeneity, in large volumes.

Ideal mixing conditions in a refolding mixture are given when the composition of the mixture with respect to its physical-chemical properties is identical at each time interval for each infinite small volume element in the refolding tank. In theory, "ideal" mixing conditions result in a homogenous solution without concentration gradients of unfolded or partially refolded protein during dilution. Ideal mixing conditions are a function of a solution's "mixing time". Mixing time is the time needed for the molecules in a droplet between addition of the droplet to the solution and their even dispersion in the total volume of the solution. Variables affecting mixing time include the total volume of the solution, the size of the added volume, the size and configuration of the mixing chamber (vessel, tank), and other characteristics of the mixing device, e.g. whether stirring occurs and which type of stirrer is used, and the location of the inlets in the mixing chamber. The larger the volume of the solution and the larger the size of the reaction vessel, the longer is the mixing time and thus the longer it takes until the mixture, e.g. the solubilized protein solution and the diluent; will not be homogenous. As reported by Ram et al. (33), mixing time in process vessels used in biopharmaceutical manufacturing can last up to several minutes.

Due to the concentration gradient present in a non-homogenous solution, there are variations of the pH value and ionic strength, which results in variations of the charges of the unfolded or partially folded protein causing the protein to refold incorrectly or interact improperly with nearby protein molecules. A high local concentration of unfolded protein in the regions of the mixing chamber where the unfolded protein is fed into the reactor, may lead to higher aggregation compared to an "ideal" mixing chamber.

In so-called "fed-batch" processes, the unfolded protein is added to the refolding tank in a semi-continuous or pulse wise manner, which results in a lower actual concentration of folding intermediates and therefore less aggregation (34). Such methods have the advantage that the actual concentration of unfolded protein is kept low, while the final concentration of refolded protein can be increased. The composition in terms of the protein's state in the refolding mixture changes from the first molecule (virtual isolation, best chance of successful folding into native conformation) to the last molecule, which is added to a volume containing the correctly folded or misfolded proteins (worst chance of successful refolding). Like in batch methods, renaturation that is conducted pulse-wise (fed-batch mode) can be only operated in a discontinuous way. In a fed-batch reactor, the amount of denaturing and reducing agents from the feed solution start to accumulate during addition of the unfolded protein until they reach a critical level at which the protein starts to unfold. Design equations for fed-batch refolding with regard to the folding and aggregation kinetics have been described by Dong et al. (35) and Kotlarsky et al. (36).

It was an object of the invention to provide an improved method for obtained a protein in its refolded, biologically active form.

The solution of the problem underlying the invention is based on refolding the protein under defined mixing conditions.

The present invention relates to a method for obtaining a biologically active recombinant protein by reconstituting the protein from a denatured state to its active form, said method containing a steps of mixing a feed solution containing the protein in its denatured form and/or its biologically inactive intermediate forms with a refolding buffer under conditions that approximate ideal mixing, wherein
  i. the mixing time is ca. 1 msec to ca. 10 sec; and
  ii. the dilution rate $F_P:F_B$ is ca. 1:1 to ca. 1:100000, wherein $F_P$ is the flow rate of said protein feed solution and $F_B$ is the flow rate of said refolding buffer.

"Denatured form", in the meaning of the present invention, designates the biologically inactive, unfolded or predominantly misfolded form of the expressed protein of interest, as obtained as a product of the recombinant production process, e.g. as obtained after dissolving the inclusion bodies.

"Intermediate forms" or "intermediates" in the meaning of the present invention, designates the forms that the protein passes through between its denatured form and its reconstituted (refolded) native and biologically active state. The intermediates, which are biologically inactive or have a lower biological activity than the native protein, may form aggregates.

A "protein" in the meaning of the present invention is any protein, protein fragment or peptide that requires refolding upon recombinant expression in order to obtain such protein in its biologically active form.

Preferred mixing times range from ca. 10 msec and ca. 5 sec, preferably from ca. 100 msec to ca. 1 sec.

By maintaining a very high flow rate of the refolding buffer and a low flow rate of the feed stream containing the unfolded protein, the method of the invention provides very high local dilution rates; preferred dilution rates range from 1:5 to 1:50000 and from 1:10 to 1:10000.

Depending on the dimensions of the system, the flow rates may vary within a wide range, e.g. from μL/min in the case of laboratory scale to Liters/min in the case of industrial scale manufacturing.

The concentration of the protein after dilution with refolding buffer is in the range of ca. 1 ng/ml to 10 mg/ml, for example ca. 100 ng/ml to ca. 5 mg/ml or ca. 1 μg/ml to ca. 1 mg/ml.

The refolding buffer used for a given protein of interest is customized to the refolding requirements/kinetics of that protein. Refolding buffers are known in the art and commercially available; typical buffer components are guadinium chloride, dithiothreitol (DTT) and optionally a redox system (e.g. reduced glutathione GSH/oxidized glutathione GSSG), EDTA, detergents, salts, and refolding additives like L-arginine.

As mentioned above, "ideal mixing" refers to conditions that result in a homogenous solution without substantial concentration gradients in solution. By ideal mixing, infinitive short mixing times are achieved.

Since the mixing conditions according to the method of the invention are close to ideal mixing, mixing of the protein feed stream with the refolding buffer occurs with similar or faster kinetics than the unfolding/aggregation kinetics of the protein, thereby reducing or completely preventing aggregation of the protein In the process of the invention, the actual protein concentration immediately after mixing is much lower as compared to conventional refolding methods.

In its simplest embodiment, the method of the invention is a batch process that comprises, as its essential step, the above-defined mixing operation, in which a feed stream having a high concentration of unfolded protein and a low flow rate is combined with a refolding buffer solution having a high flow rate.

Figure 1:
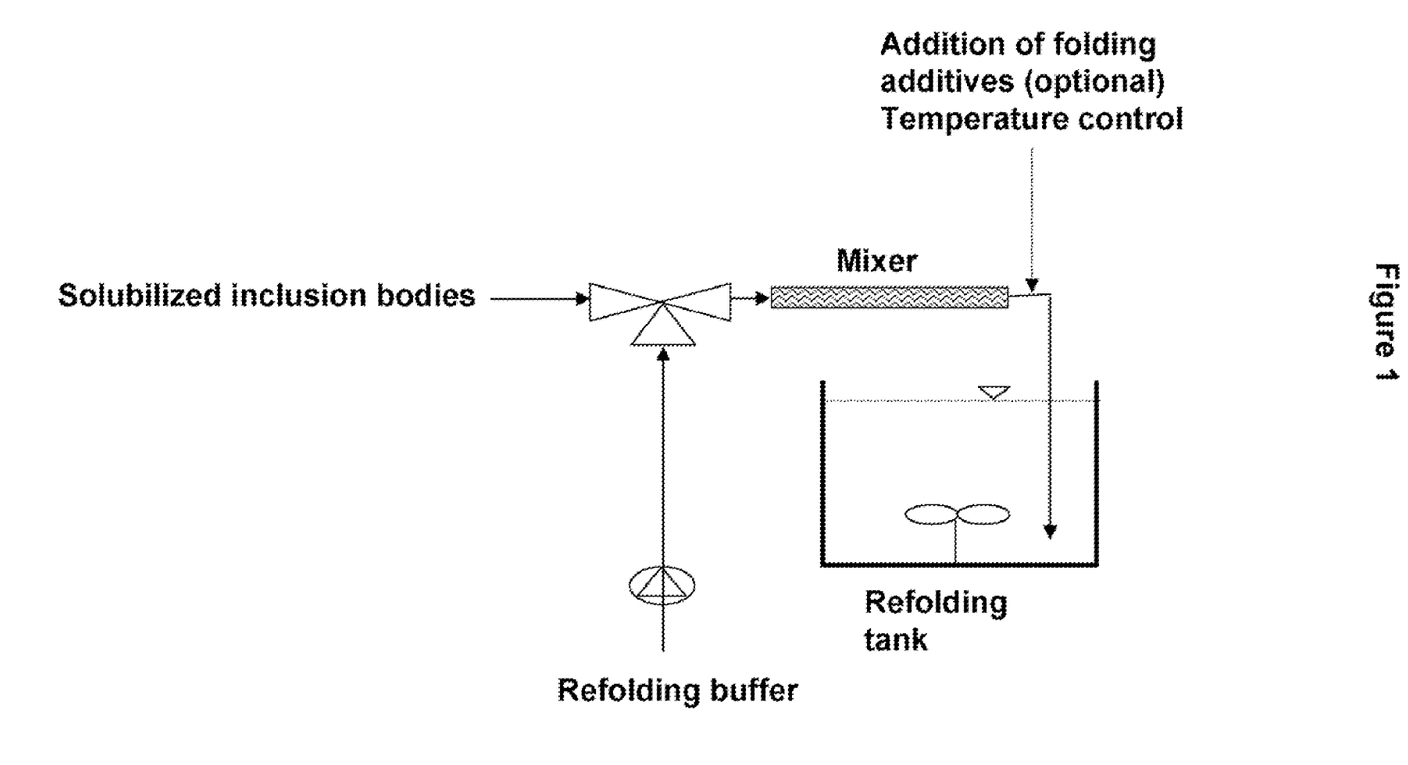
FIG. 1: Setup for fast mix refolding in its simplest form

This embodiment of the invention, which is schematically shown in FIG. 1, is particularly useful for proteins that have very fast refolding kinetics, e.g. peptides and smaller protein fragments. The refolding buffer and the protein feed solution are independently fed from reservoirs to the mixing device. Having passed the mixing device, the highly diluted solution containing the refolded protein is collected in a tank. Optionally, before entering the tank, refolding additives may be added in the case of proteins that have not yet completely refolded during mixing to suppress or completely prevent unfolding/aggregation. Compounds useful as refolding additives are known in the art, examples are L-arginine, Tris, detergents, redox systems like GSH/GSSG, ionic liquids like N'-alkyl and N'-(omega-hydroxy-alkyl)-N-methylimidazolium chlorides etc. The end of the process is reached when the reservoir of refolding buffer and/or protein solution is exhausted. At this point, the feed of unfolded protein (or the feed of buffer, respectively) is interrupted and the solution containing the protein in its refolded, biologically active form is withdrawn from the tank. In this embodiment of the invention, it is advantageous to have the mixing device equipped with means that control the temperature to exclude any, even minimal aggregation, e.g. cooling means.

Mixing devices suitable for use in the method of the invention are any mixers that ensure fast mixing and short mixing times, e.g. tubular jet mixers or static mixers, e.g. commercially available mixers from Fluitec, CH, or Sulzer Chemtech, CH. In the simplest form of the method of the invention, the two streams can be combined into one stream by a branch connection without any additional specific mixing devices. Such a simple device can be used to achieve the desired mixing efficiency, albeit without precise control of mixing efficiency. In the case that the mixer is a high-throughput continuous flow device, accurate control of the flows is of particular importance. With such mixers, mixing times as low as a few milliseconds on the small scale or a few seconds on the large scale can be achieved. The mixing characteristics of such mixers most closely approximate "ideal mixing". The mixing ratio of the two streams is adjusted such that a low protein concentration is maintained to minimize aggregation. After mixing the two streams, the protein starts to refold.

The method of the invention is also referred to as "fast mix refolding".

Except for proteins with fast refolding kinetics, which may already be completely refolded during mixing, the initial refolding steps take place in the mixing device and refolding is completed in the refolding tank or in the optionally present adjustment zone, e.g. in the plug flow reactor (PFR), as described below.

In a further embodiment, the method of the invention comprises in addition, subsequent to the mixing step defined above and before the solution enters the refolding tank, a step in which the highly diluted mixture is transferred to a zone in which the protein is allowed to form more stable folding intermediates under precisely controlled conditions such that unfolding and formation of aggregates is suppressed or completely prevented. This step is also referred to as "adjustment step", and the zone or the reactor in which adjustment occurs is referred to as "adjustment zone" or "adjustment reactor", respectively.

In a preferred embodiment, the adjustment reactor is a plug flow reactor, i.e. a chemical reactor where the fluid passes through in a coherent manner, so that the residence time is the same for all elements. An ideal plug flow reactor has a fixed residence time:

Any fluid that enters the reactor at time t will exit the reactor at time t+τ, where τ is the residence time of the reactor. In its simplest form, the plug flow reactor is a tube, optionally packed with solid material.

The adjustment step provides the possibility of generating, for a defined volume and period of time, conditions that favor stabilization of the partially refolded protein. This may be achieved by a short-term change of the pH value (increase or decrease) and/or change of the temperature (heating or cooling) and/or addition of refolding additives, as defined above, in the adjustment zone. The adjustment step provides the advantage that optimal refolding conditions, e.g. heating or cooling or addition of additives, need to applied only to a small volume as compared to the refolding tank, thus saving energy, reagents and costs.

The mean residence time, i.e. the time that it takes for the solution to pass through the adjustment reactor, i.e. the tube in the case of a plug flow reactor, depends on the flow rate and the tube volume. The residence time should be long enough to allow the protein to fold into a more compact and stable structure, e.g. into a so-called 'molten globule' intermediate.

By varying the design of the adjustment reactor, e.g. length and/or diameter of the tube, the residence time of a specific protein in the adjustment zone and thus its exposure to the selected adjustment conditions is adapted to the requirements of the protein, i.e. its specific refolding kinetics. In the case of fast refolding kinetics, refolding is usually completed already in the adjustment zone.

After leaving the adjustment zone, the protein solution containing the refolded protein and/or the partially refolded stabilized intermediates is collected in the refolding tank, where, if still necessary, refolding is completed.

In the embodiment that provides an adjustment step, the method of the invention may be conducted batch-wise or preferably, by recycling the protein solution from the refolding tank, in the fed-batch mode.

Figure 2:
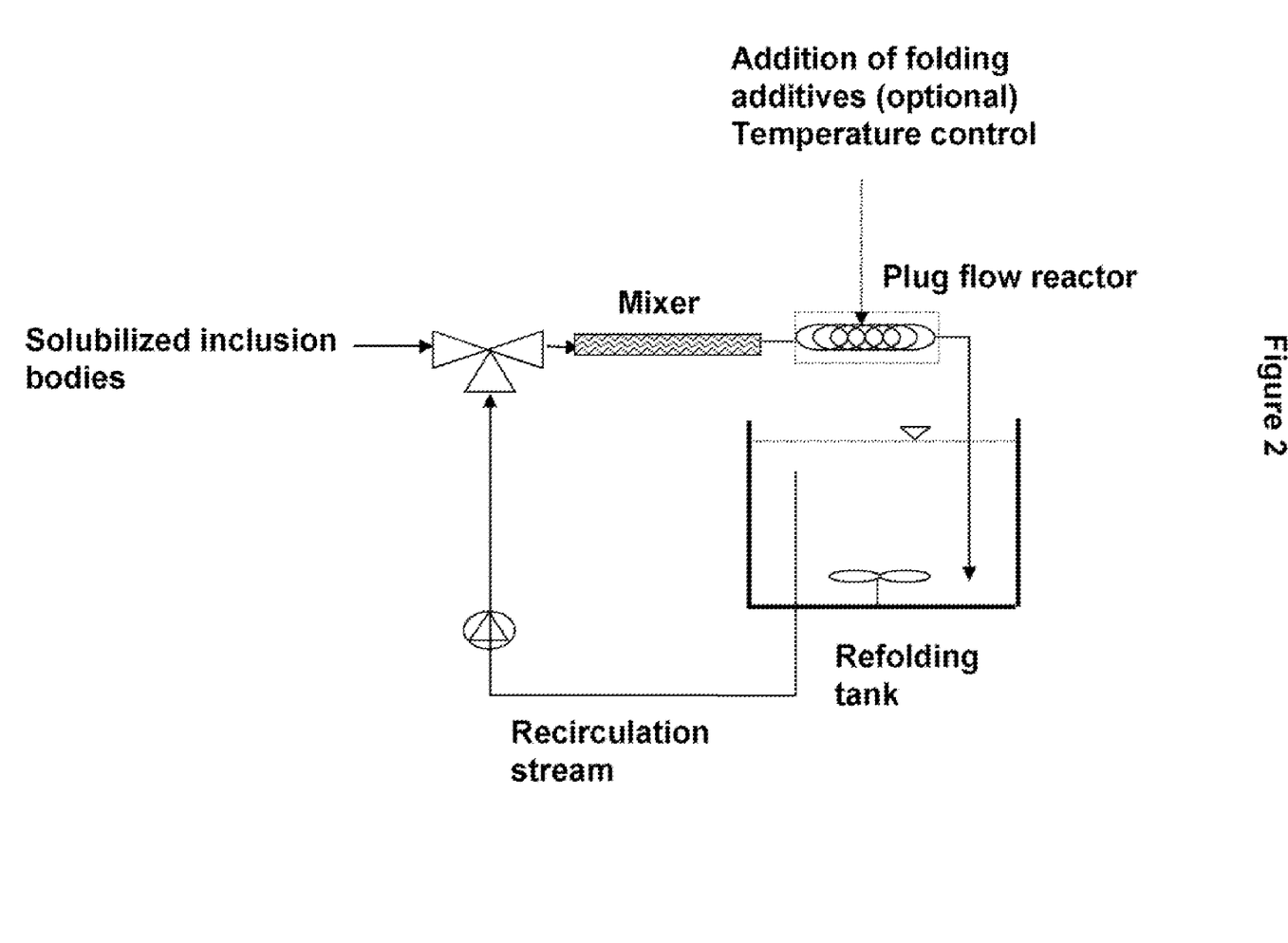
FIG. 2: Setup for fast mix refolding, including an adjustment zone and recycling of the refolded protein

In the batch mode, the end of the process is reached when the reservoir of refolding buffer and/or protein solution is exhausted. At this point, the feed of unfolded protein, or of the refolding buffer, respectively, is interrupted and the protein solution is withdrawn from the tank. FIG. 2 shows the schematic drawing of the embodiment of the invention that is a fed-batch process comprising an adjustment step in combination with recycling of the protein solution. In this embodiment, the protein solution circulates at high flow rates from the refolding tank back to the feed inlet, where unfolded protein is freshly introduced into the system. In such embodiment, the recycled protein solution forms the refolding buffer solution.

In a preferred embodiment, the method of the invention is performed on-line and, even more preferred, in a continuous mode. "On-line" means that refolding is connected to one or more other steps, e.g. antecedent steps, of the overall process, e.g. solubilization of inclusion bodies.

Figure 3:
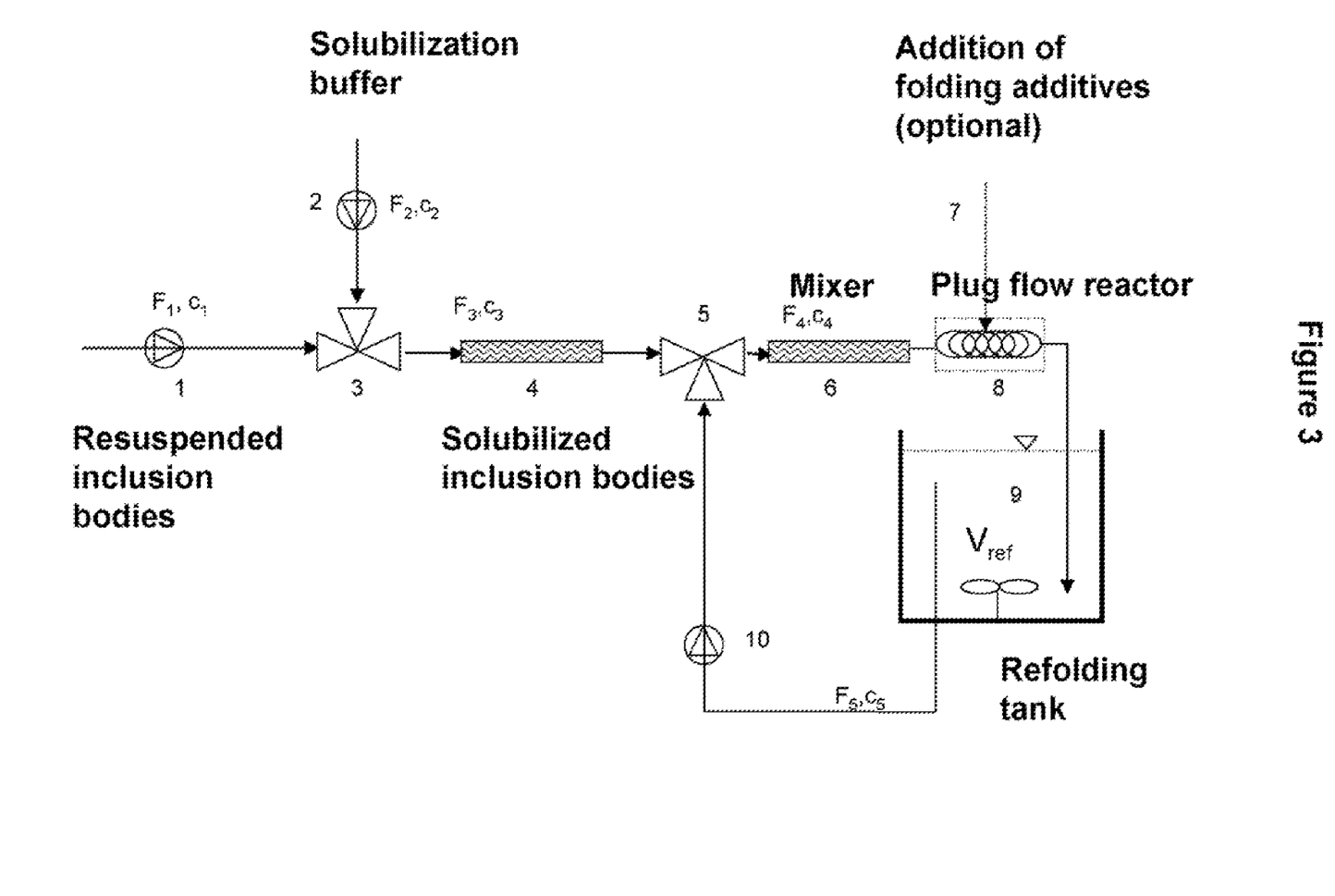
FIG. 3: Setup for continuous fast mix refolding in combination with on-line solubilization of inclusion bodies
1) feed pump delivering the resuspended inclusion bodies;
2) solubilization buffer pump; 3, 5) branch connection;
4, 6) mixing device; 7) addition of folding additives (optional); 8) plug flow reactor; 9) refolding mixture vessel; 10) recirculation pump

By running refolding continuously and on-line with solubilization of inclusion bodies, as depicted in FIG. 3, time consumption and costs can be reduced and the yield of refolded protein increased as compared to known methods. The method of the invention ensures, in particular in its continuous on-line embodiment, fast and efficient processing of inclusion body proteins, thereby reducing inadvertent variations, such as variations in refolding efficiency or product homogeneity. On-line solubilization of suspended inclusion bodies is preferred to their batch-wise solubilization in a stirred tank, where the contact time between the molecules and the solubilizing agent has to be minimized or precisely controlled to avoid irreversible modification of the proteins. This is often the case when solubilization of the inclusion bodies is carried out at extreme pH values. Such irreversible modification of amino acid side chains could lead to reduced activity of the molecule.

Exemplified by the embodiments in which the protein solution is recycled (FIGS. 2 and 3), very high local dilution rates (1:1000, 1:10000 or more) can be easily achieved depending on the ratio of the flow rate of the solution of unfolded protein $F_B$ (designated $F_3$ in the Figure) and the flow rate of the circulating refolding buffer $F_B$ (designated $F_5$ in the figure). The protein concentration $C_4$ after dilution can be calculated by a simple mass balance as $$C_3F_3 + C_5F_5 = C_4F_4 \text{ and } F_4 = F_3 + F_5$$

$C_3$ is the concentration of the unfolded protein in the feed stream and $C_4$ is the concentration of unfolded protein immediately after mixing. The flow rate of the circulating stream necessary to achieve the desired concentration of unfolded protein after dilution ($C_4$) can be simply calculated by neglecting $C_5$ (refolded protein present in the reaction system, which is less susceptible to aggregation) as $$F_5 = ((C_3 \times F_3)/C_4) - F_3$$

The total protein concentration in the reaction system increases between the addition of the unfolded protein and the time point when the desired final concentration is reached, e.g. at 1 μg/ml/min. Addition of the solution of unfolded protein is either stopped when the desired concentration is reached or when the concentrations of denaturing and reducing chemicals of the feed stream exceed a value that is critical for the protein to unfold.

The volume of refolding buffer solution $V_{ref}$ in the refolding tank prior to starting the addition of the unfolded protein stream depends on the desired final protein concentration in the reactor ($C_5$) after complete processing the unfolded protein solution $V_{denat}$ and can be calculated by $$V_{ref} = ((C_3 \times V_{denat})/C_5) - V_{denat}$$

When addition of the desired volume/amount of unfolded protein is completed, the solution can be further incubated in the refolding tank to allow complete refolding of the protein. The time period for such subsequent refolding depends on the refolding kinetics of the protein.

In the continuous mode, the refolding solution circulates via an additional pump back to the inlet of the feed solution containing unfolded protein. Depending on the flow rate of the feed stream and the flow rate of the refolding solution, high dilution rates can be achieved after mixing of the two streams. This effect and the continuous supply of the unfolded protein (or approximately continuous by fed-batch addition, respectively) result in higher conversion of unfolded protein into the native, biologically active protein as compared to batch or fed-batch refolding without recirculation Addition of the feed solution is stopped when the concentration of denaturing agents from the feed stream, e.g. urea or DTT, has reached a critical threshold value.

Particularly in the continuous mode, precise control of the dilution step (protein concentration, mixing time) as well as residence time and selected refolding parameters in the adjustment zone allow a more efficient renaturation of the protein as compared to the known batch or fed-batch dilution methods.

The feed has been obtained from fermentation of bacterial, yeast, fungal, plant or animal cells carrying an expression vector to produce a heterologous protein of interest. The feed is a protein solution, usually obtained from solubilization of the inclusion bodies. In the on-line mode of the method of the invention, the feed stream, when it enters the system, contains the resuspended inclusion bodies, which are solubilized on-line before the protein feed is combined with refolding buffer and enters the mixing zone.

The protein feed contains, besides buffer substances, components that promote the solubilization of inclusion bodies, e.g. chaotropic agents such as urea, guanidinium chloride (GdmCl), sodium and/or potassium thiocyanate, and reducing agents such as mercaptoethanol, dithiothreitol, monothioglycerol. Suitable compositions and conditions for solubilization of inclusion bodies are known in the art, they have been extensively described in the literature (11; 12; 37).

In a final step, the protein is separated and purified according to methods known in the art, including, but not limited to, dialysis, filtration, extraction, precipitation and chromatography techniques.

EXAMPLE

Refolding of α-lactalbumin

Bovine α-lactalbumin (α-LA) (38) is used as a model protein. The native protein contains 123 amino acid residues (Mr 14176) and four disulfide bonds. The oxidative folding pathway is well characterized and the protein has an additional calcium-binding site, which increases the stability of the native protein (39) and is thus well suited as a model protein. The protein goes through a molten globule folding state as determined by stopped-flow X-ray scattering (16). The kinetic folding intermediate of α-LA has a native-like secondary structure in the α-domain and a loose hydrophobic core accessible to solvent, bur lacks most of the specific side-chain packing.

Preparation of Denatured and Reduced Protein

For refolding experiments, α-LA is denatured and reduced in a refolding buffer containing 0.1 M Tris-HCl, pH 8.0, 6 M GdmHCl, 1 mM EDTA and 20 mM DTT and incubated for 1 h at room temperature. The concentration of denatured protein is analyzed by RP-HPLC as described below.

Refolding by Dilution

Denatured and reduced aliquots at 16.5 mg/ml are rapidly diluted (batch-dilution) 32 fold into renaturation buffer consisting of 100 mM Tris-HCl, 5 mM $CaCl_2$, 2 mM cystine and 2 mM cysteine, pH 8.5, to a final protein concentration of 0.516 mg/ml. The refolding volume is 2 ml.

In fed-batch refolding (pulse renaturation), 6.25 ml of the feed solution are fed over a time period of 90 min (flow rate of 70 μl/min) into refolding buffer. The final refolding volume is 200 ml.

Refolding according to the method of the present invention (fast mix refolding) is done by feeding 6.25 ml of unfolded protein solution at a flow rate of 0.434 ml/min to the recirculating refolding buffer stream (80 ml/min). The two streams are combined via a branch connection and mixed in a static mixing device (Sulzer Chemtech, Germany). The mixing device had a hold-up volume of 1.25 ml. The mixing time is less than one second as determined with a test solution containing bromphenol blue as tracer substance. The outlet of the mixer is connected to a plug flow reactor in the form of a silicone tubing (5 mm inner diameter×80 cm) resulting in a mean residence time of 12 sec. The refolding mixture is then collected in a stirred glass vessel and continuously re-circulated.

Samples are drawn after various time intervals and analyzed for native protein by RP-HPLC and circular dichroism (CD).

Quenching of Oxidative Refolding

The kinetic of the oxidative refolding process is monitored by removing 100 μl samples at specific time intervals and quenching the formation of disulphide bonds by addition of 15 μl 6.4% HCl, resulting in pH 2.

Analytical Methods

Prior to analysis, all samples are centrifuged at 12.000 g for 3 min to remove insoluble material. For RP-HPLC a C4 column (Vydac 214TP54) is connected to an Agilent 1100 HPLC system (Agilent Technologies). Fully denatured α-LA is separated from oxidative folding intermediates and native protein by linear gradient elution from 36% to 45% acetonitrile/water containing 0.1% TFA in 30 min at 1 ml/min and 30° C. The system is calibrated with solutions of native and denatured α-LA. No difference in absorbance at 214 nm is detected for equivalent amounts of injected samples of native and fully reduced protein. For determination of total protein samples are denatured and reduced by 1:6 dilution in 0.1 M Tris-HCl, 6 M Gdn HCl, 50 mM DTT and 1 mM EDTA, pH 8.0, and analyzed by RP-HPLC. When the refolded protein eluted at the same position as the native protein standard, we assumed that the protein is in its native conformation. The completely unfolded and reduced protein exhibits a higher retention time compared to the native protein.

Far UV CD spectra of native, refolded and denatured α-LA are recorded on a Jasco J-600 spectropolarimeter. The CD spectra of native and refolded protein are measured in 2 mM phosphate buffer pH 7.7 containing 1 mM $CaCl_2$ at 25° C. Protein concentrations are 90 μg/ml. Far-UV wavelength scans are performed in a 1 mm quartz cuvette using five repeats with an averaging time of 4 s at each wavelength and a spectrometer bandwidth of 1.0 nm. All spectra are averaged and smoothed taking the mean of the five data points. Due to the high amount of Gdn-HCl in the denatured protein sample, significant data could not be recorded at wavelengths below 215 nm.

Results

Figure 4:
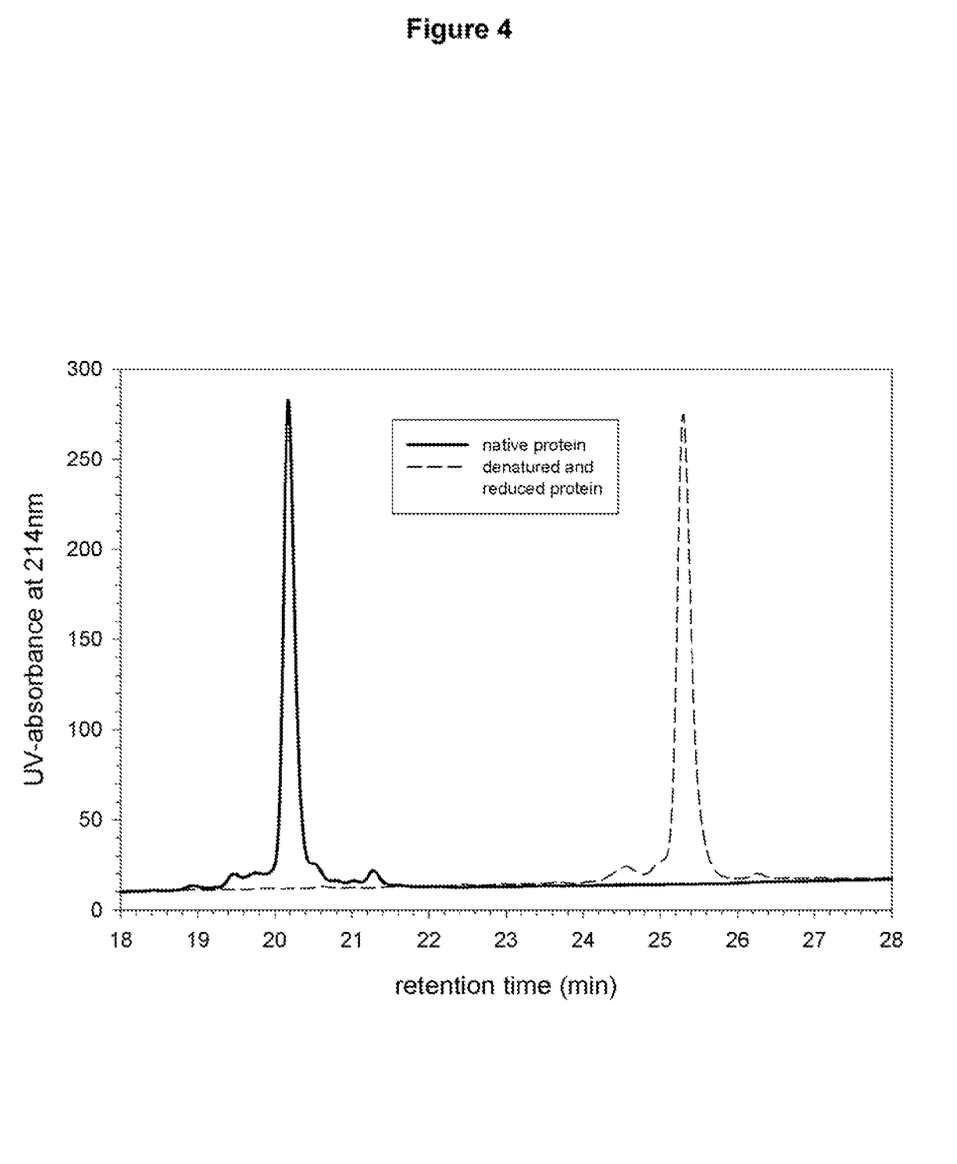
FIG. 4: Reversed phase HPLC chromatogram of native and denatured and reduced α-lactalbumin
Figure 5:
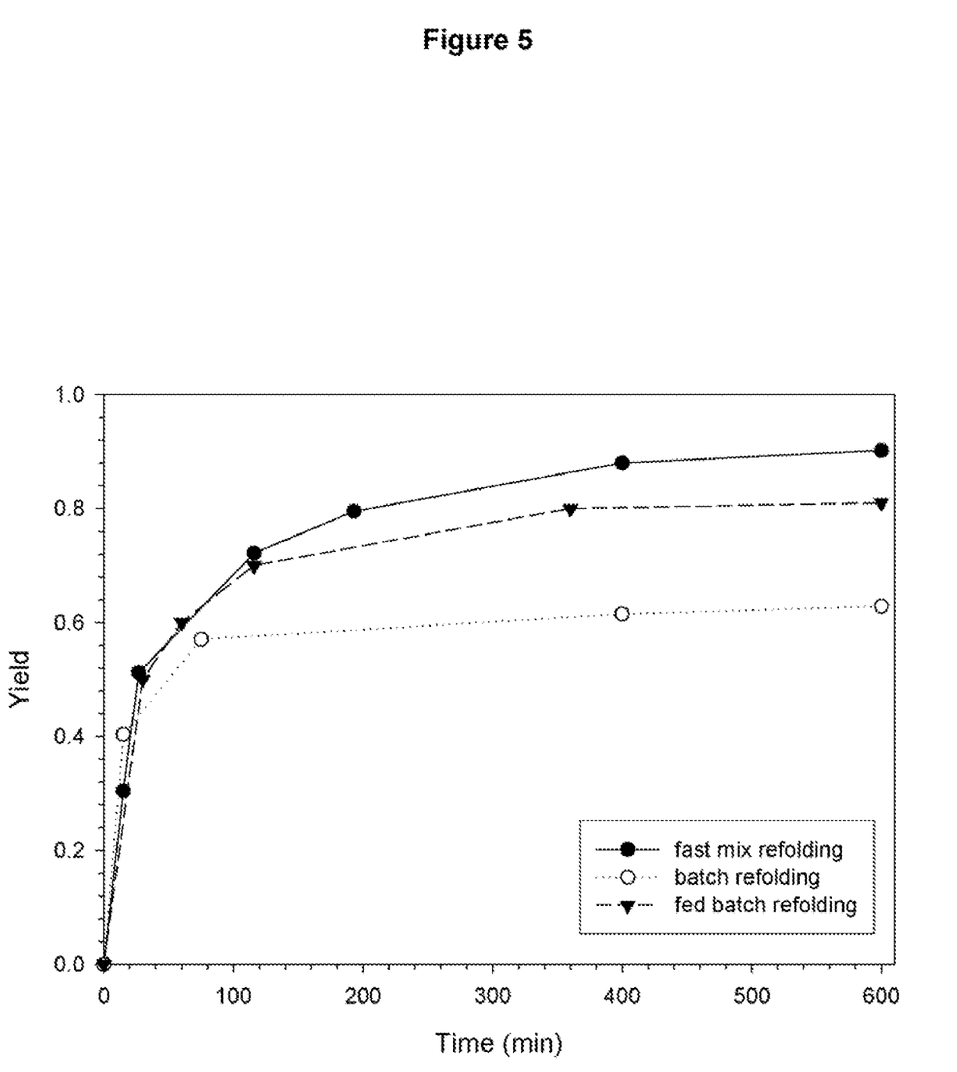
FIG. 5: Time course of protein refolding in a batch, fed-batch and fast mix refolding reactor

Refolding experiments with the model protein α-LA at a final protein concentration of approx. 0.5 mg/ml are carried out. Samples are quenched after various time intervals and analyzed by RP-HPLC (see FIG. 4) for refolded protein. The time course of protein refolding during conventional batch and fed-batch methods on the one hand and fast mix refolding on the other hand is shown in FIG. 5. The final yield of refolded protein at equilibrium is 63% for the batch system and 81% for the fed-batch system. Using the fast mix refolding method of the present invention, the yield of refolded protein is 90%. In all experiments, the final dilution rate of the unfolded protein and refolding buffer is 32 fold. The temporary dilution rate as calculated as the ratio of the circulating folding buffer and feed stream is 184. The unfolded protein concentration after mixing of the two streams is therefore approx. 3 μg/ml followed by a 13 sec hold up time in a plug flow reactor. Within this period of time, the unfolded protein collapses and forms folding intermediates, which are less susceptible to aggregation.

Figure 6:
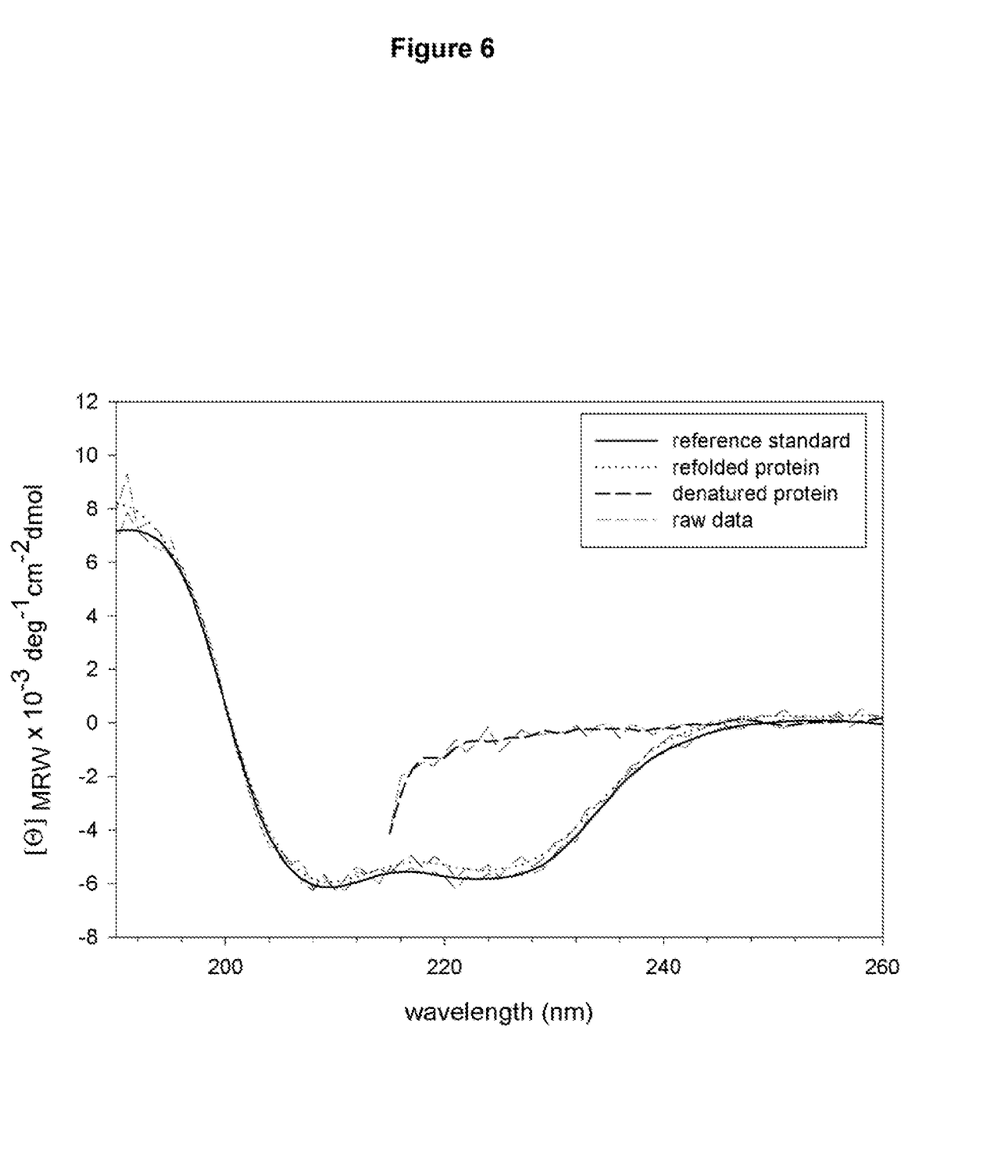
FIG. 6: CD spectroscopic analysis of native, refolded and denatured α-lactalbumin

Native conformation of refolded protein is also confirmed by circular dichroism (see FIG. 6). The spectra of the refolded and native protein are identical, whereas the unfolded protein shows a completely different spectrum. The CD spectra of the refolded and native protein resemble those published by Wu et al. (39).

The invention claimed is:

1. A method for obtaining a biologically active recombinant protein by reconstituting the protein from a denatured state to its active form, said method comprising the step of mixing a stream of feed solution containing the protein in its denatured form and/or its biologically inactive intermediate forms with a stream of refolding buffer under conditions that approximate ideal mixing, wherein
   i. the mixing time is about 1 msec to about 10 sec; and
   ii. the dilution rate $F_P:F_B$ is about 1:5 to about 1:50000, wherein $F_P$ is the flow rate of said protein solution and $F_B$ is the flow rate of said refolding buffer.

2. The method of claim 1, wherein said mixing time is about 10 msec to about 5 sec.

3. The method of claim 2, and wherein the mixing time is about 100 msec to about 1 sec.

4. The method of claim 1, wherein the dilution rate about 1:10 to about 1:10000.

5. The method of claim 1, wherein the concentration of the protein after mixing with the refolding buffer is between about 1 ng/ml and about 10 mg/ml.

6. The method of claim 5, wherein the concentration of the protein is between about 100 ng/ml and about 5 mg/ml.

7. The method of claim 6, wherein the concentration of the protein is between about 1 μg/ml and about 1 mg/ml.

8. The method of claim 1, wherein the protein solution obtained after mixing is collected in a tank and incubated until the protein is completely present in its biologically active form.

9. The method of claim 1 or claim 8, comprising, subsequent to said mixing step, a step wherein the protein solution is adjusted to conditions that favor refolding of the protein.

10. The method of claim 9, wherein said adjusting comprises increasing or decreasing the temperature and/or increasing or decreasing the pH value and/or adding refolding additives.

11. The method of claim 9, wherein said adjustment step is carried out in a plug flow reactor.

12. The method of claim 9, wherein the protein solution is recycled from the tank and combined with said protein feed solution.

13. The method of claim 12, wherein said protein feed solution has been obtained by solubilization of inclusion bodies.

14. The method of claim 13, wherein said solubitization is on-line.

15. The method of claim 14, which is run continuously.

* * * * *